United States Patent [19]

Kawasaki et al.

[11] 4,363,813

[45] Dec. 14, 1982

[54] 2-(3,4,5-TRIMETHOXYPHENYL)-4,5-DISUB-STITUTED THIAZOLES

[75] Inventors: Takao Kawasaki, Sayama; Yoshiaki Osaka, Nagareyama; Tadashi Tsuchiya, Matsudo, all of Japan

[73] Assignee: Kureha Kagaku Kogyo Kabushiki Kaisha, Nihonbashi, Japan

[21] Appl. No.: 163,507

[22] Filed: Jun. 27, 1980

[30] Foreign Application Priority Data

Jul. 9, 1979 [JP] Japan .................................. 54-87055
May 23, 1980 [JP] Japan .................................. 55-68507

[51] Int. Cl.$^3$ .................. C07D 233/54; A61K 31/425
[52] U.S. Cl. .................................... 424/270; 548/202; 548/203; 548/204

[58] Field of Search ...................... 548/202, 203, 204; 424/270

[56] References Cited

U.S. PATENT DOCUMENTS

| | | | |
|---|---|---|---|
| 1,743,083 | 11/1930 | Johnson | 260/44 |
| 1,970,656 | 8/1934 | Johnson | 548/203 |
| 2,014,498 | 9/1935 | Johnson | 260/44 |
| 2,030,373 | 2/1936 | Johnson | 260/44 |
| 4,154,947 | 5/1979 | Goldman | 542/412 |

*Primary Examiner*—Nicholas S. Rizzo
*Attorney, Agent, or Firm*—Wegner & Bretschneider

[57] ABSTRACT

2-(3,4,5-trimethoxyphenyl)-4,5-disubstituted thiazoles, each of which has an anti-peptic ulcer activity, and methods for producing the same are disclosed herein.

4 Claims, No Drawings

2-(3,4,5-TRIMETHOXYPHENYL)-4,5-DISUBSTITUTED THIAZOLES

DETAILED EXPLANATION OF THE INVENTION

The present invention relates to novel chemical compounds 2-(3,4,5-trimethoxyphenyl)-4,5-disubstituted thiazoles.

The novel chemical compounds, 2-(3,4,5-trimethoxyphenyl)-4,5-disubstituted thiazoles according to the present invention are useful as an active ingredient of anti-peptic ucler medicines.

2-(3,4,5-trimethoxyphenyl)-4,5-disubstituted thiazoles according to the present invention are represented by the following general formula (I):

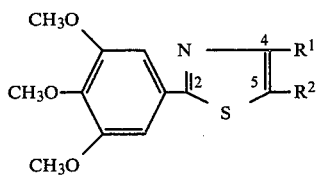

wherein $R^1$ represents an alkyl group of $C_1$ to $C_3$, and $R^2$ represents a hydrogen atom, an alkyl group of $C_1$ to $C_3$, acetyl group, carbamoyl group, hydrazinocarbonyl group, carboxyl group, esterified carboxyl group by lower alcohol of $C_1$ to $C_3$ or further acetyl group in which the carbonyl group has been converted to C=NOH group, C=NOCOCH$_3$ group, C=N—NH—CONH$_2$ group, C=N—NHCSNH$_2$ group or C=NHC(NH)NH$_2$ group with a proviso that both $R^1$ and $R^2$ are not hydrogen atoms simultaneously.

2-(3,4,5-trimethoxyphenyl)-4,5-disubstituted thiazoles according to the present invention include the following compounds: 2-(3,4,5-trimethoxyphenyl)-4-methyl-5-acetylthiazole, 2-(3,4,5-trimethoxyphenyl)-4-methyl-5-acetylthiazole-oxime, 2-(3,4,5-trimethoxyphenyl)-4-methyl-5-acetylthiazole-oxime acetate, 2-(3,4,5-trimethoxyphenyl)-4-methyl-5-acetylthiazole-thiosemicarbazone, 2-(3,4,5-trimethoxyphenyl)-4-methyl-5-acetylthiazoleguanylhydrazone, 2-(3,4,5-trimethoxyphenyl)-4-methylthiazole-5-carboxylic acid ethyl ester, 2-(3,4,5-trimethoxyphenyl)-4-methyl-5-thiazolecarboxylic acid hydrazide, 2-(3,4,5-trimethoxyphenyl)-4-methyl-5-thiazolecarboxylic acid, 2-(3,4,5-trimethoxyphenyl)-4-methylthiazole, 2-(3,4,5-trimethoxyphenyl)-4-methylthiazole-5-carboxylic acidamide, 2-(3,4,5-trimethoxyphenyl)-4,5-dimethylthiazole and 2-(3,4,5-trimethoxyphenyl)-4-ethyl-5-methylthiazole.

2-(3,4,5-trimethoxyphenyl)-4,5-disubstituted thiazoles according to the present invention (hereinafter referred to as the present compounds) are synthesized by various methods corresponding to their kinds, for instance, as follows:

(a) A synthetic method shown below:

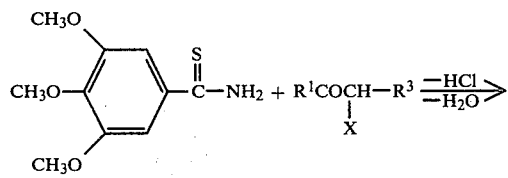

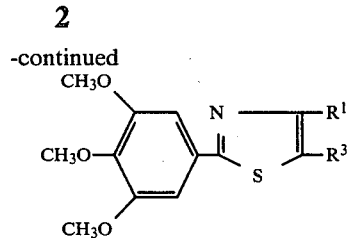

wherein $R^1$ represents an alkyl group of $C_1$ to $C_3$, $R^3$ represents a hydrogen atom, alkyl group of $C_1$ to $C_3$, acetyl group or ethoxycarbonyl group and X represents a halogen atom such as chlorine and bromine.

The above-mentioned reaction (a) is cyclization to a thiazole ring by the condensation of trimethoxythiobenzamide and aplpha-halogenoketone.

The above-mentioned reaction proceeds in an inert solvent used in an ordinary organic reactions, such as benzene, toluene and xylene by heating trimethoxythiobenzaldehyde and alpha-halogenoketone in a little excessive amount at a temperature of 20° to 200° C., preferably 50° to 150° C. for one to ten hours. Since in the above-mentioned reaction, both dehydration and dehydrochlorination occur, the rate of reaction and the yield of the product are raised by removing the water formed during the reaction in utilizing azeotropism at a boiling temperature of the aqueous solvent or by adding in advance a dehydrochlorinating agent such as sodium carbonate and magnesium oxide.

Furthermore, since trimethoxythiobenzamide is expensive, another reaction may be adopted in which, instead of trimethoxythiobenzamide, trimethoxybenzamide and diphosphorus pentasulfide are added into the reaction system and the system is heated at 50°–150° C. to form trimethoxythiobenzamide in advance and then alpha-halogenoketone is added to proceed the reaction.

After the reaction is over, the reaction mixture is cooled to separate the thus formed crystalline thiazole. The separated crystals are collected by filtration and purified by recrystallization using a solvent usually used for recrystallization, for instance, water, methanol, ethanol, acetone, ethyl acetate, benzene or their mixture.

(b) A synthetic method shown below:

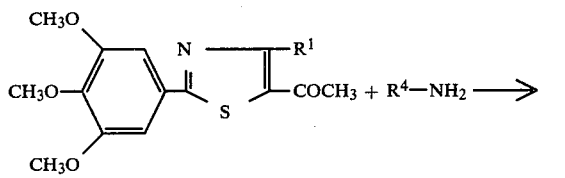

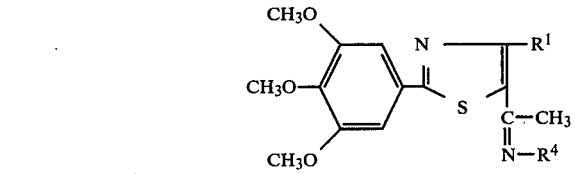

wherein $R^4$ represents —OH,

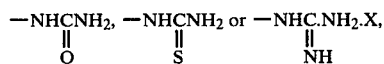

and X represents one equivalent amount of an acid, $R^1$ meaning the same as in (I).

The above-mentioned reaction (b) proceeds in ethanol or an aqueous ethanolic solution by heating at a temperature of 50° to 100° C. for one to 10 hours. The reaction mixture may be acidic, neutral or alkaline.

(c) A synthetic method shown below:

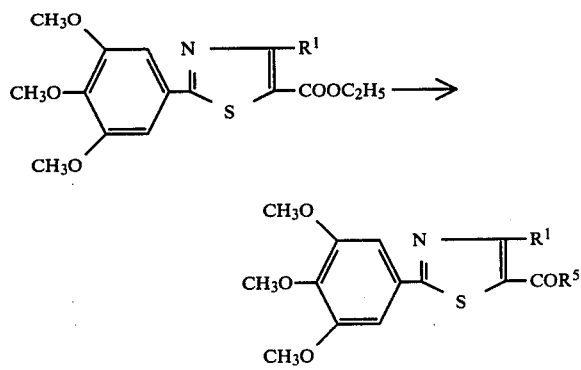

wherein $R^5$ represents —OH, —$NH_2$ or —$NHNH_2$ and $R^1$ means the same as in (I).

In the above-mentioned reaction (c), 2-(3,4,5-trimethoxyphenyl)-4-alkyl of $C_1$ to $C_3$-thiazole-5-carboxylic acid ester obtained by the method (a) is used as a starting material and by hydrolysing this compound with sodium hydroxide in an aqueous ethanolic solution, the corresponding thiazole-5-carboxylic acid is prepared, or by bringing the above-mentioned starting material into reaction with ammonia in an aqueous ethanolic solution, the corresponding thiazole-5-carboxylic acidamide is obtained, or further, by bringing the above-mentioned starting material into reaction with hydrazine hydrate in an aqueous ethanolic solution, the corresponding thiazle-5-carboxylic acid hydrazide is obtained.

(d) A synthetic method shown below:

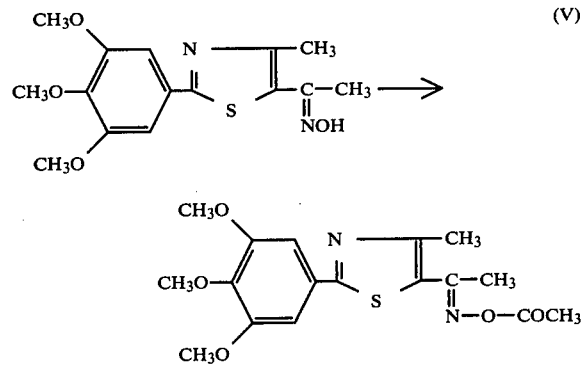

(V)

In the above-mentioned reaction (d), 2-(3,4,5-trimethoxyphenyl)-4-alkyl of $C_1$ to $C_3$-5-acetylthiazole-oxime obtained by the above-mentioned method (b) is acetylated by acetic anhydride to give 2-(3,4,5-trimethoxyphenyl)-4-alkyl of $C_1$ to $C_3$-5-acetylthiazole-oxime acetate.

The novel chemical compounds according to the present invention have superior anti-peptic ulcer activity to that of the hitherto known anti-peptic ulcer medicine, and on the other hand, the toxicity of the above-mentioned novel compounds is extremely low, and accordingly, the novel chemical compounds of the present invention are useful as an active ingredient of anti-peptic ulcer medicines.

The followings are the explanation of pharmacological and toxico-logical properties of the present compounds:

The important problem in developing a new anti-peptic ulcer medicine is in the screening system of the candidate anti-peptic ulcer medicine. Hitherto, the evaluation of candidate anti-peptic ulcer medicine has been carried out based on their prophylactic effect against an acute peptic ulcer such as Shay's ulcer and peptic ulcer artificially induced by aspirin or indomethancin.

However, to what extent does the results of screening carried on such models of peptic ulcer reflect the curing effect in human peptic ulcer of the candidate medicine has not been sufficiently elucidated.

The inventors of the present invention, taking into account of these situations, added to the above-mentioned method of evaluation the effect of accelerating the curation of the peptic ulcer by orally administering the present compound and a commercialized anti-peptic medicine, respectively to rats to which duodenal peptic ulcer induced by acetic acid (refer to Okabe, Americ. J. Dig. Dis. Vol. 16, p. 277, 1971) considered to be most closely resembling to human peptic ucer has been artificially formed.

According to the above-mentioned method for evaluation, effectiveness is not seen in the antacid medicine and the anti-choline medicine which have been hitherto used as an anti-peptic medicine, and the effectiveness is only a little seen in gefarnate which has been called as a tissue-repairing medicine.

Whereas, in the groups of experimental animals to which the present compound was administered, a remarkable curing effect was obtained, and in the histological findings on the region of peptic ulcer, almost complete healing state was confirmed. The followings are the concrete explanation of pharmacological effect of the present compound:

Anti-peptic ulcer action of the present compound:

Some of the anti-peptic ulcer functions are summarized, as follows: For instance, in the test carried out on rats with their pylorus ligated following Shay et al. Gastroenterology, Vol. 5, p. 43, (1945), the present compound showed a rate of suppressing the occurrence of peptic ulcer of 70 to 90% by an intraperitoneal administration of 100 mg/kg whereas a commercialized anti-peptic ulcer medicine, gefaranate, showed the rate of suppression of only about 11% at the same dose level.

Moreover, in another test using rats artificially suffering from peptic ulcer induced by acetic acid, which is said to be most closely resembling to human peptic ulcer (refer to Okabe, Americ. J. Dig. Dis. Vo. 16, p. 277, 1971), the present compound showed a rate of cure of 60 to 90% at a dose rate of 100 mg/kg, whereas the above-mentioned medicine, gefarnate, showed a rate of cure of only 23% at the same dose level.

In this connection, the above-mentioned experimental model of artificial peptic ulcer on rats has been highly evaluated internationally as a method for screening candidate anti-peptic ulcer agents as compared to the method of forming ulcer by cauterization (refer to Skoryna, Gastroenterology, Vol. 34, p. 1, 1958) and the method of forming ulcer by administering cortizone on the clamped organ (refer to Umehara, Chiryo, Vol. 47, p. 397, 1965) because the thus formed ulcer is scarcely curable in nature and the histopathological changes occurring at the ulcer region closely resemble to those of human chronic peptic ulcer.

In addition, the present compound shows superior effects to the effects of commercialized anti-peptic ulcer medicine on the evaluation by the hitherto broadly utilized effective methods for clinically screening candidate anti-peptic ulcer agents such as the method of inducing ulcer by stress and the method of inducing ulcer by aspirin.

Toxicological properties of the present compound:

According to the results of acute toxicity tests using rats and mice as experimental animals, $LD_{50}$ p.o. of each of the present compounds was larger than 5 g/kg on rate and mouse, and $LD_{50}$ i.v. was larger than 1.5 g/kg on rat and mouse.

Moreover, a group of mice were reared with the feed containing one of the present compounds for 3 months, and during the period, the general symptoms, the transition of body weight and the amount of feed intake of the mice were observed. The average intake of the present compound was 400 mg/kg/day with a small deviation. In all items of physical examination, the difference between those mice taken the feed containing the present compound and those taken the feed not containing the present compound was negligibly small.

After ending the above-mentioned breading, the mice were sacrificed and their major organs including the liver, kidney, heat, spleen, etc. were examined by naked eyes and were prepared to the tissue specimens to be microscopically examined. The specimens of their blood and urine, collected on sacrification, were biochemically examined. In these examinations, no abnormal finding were recognized.

As are shown above and as will be seen in Example 16, it was confirmed that the safety of the present compound was remarkably high enough to be administered as an anti-peptic ulcer medicine for human cases.

In the next place, the manufacture of medicinal preparations for use as anti-peptic ulcer medicines containing the present compound as an active ingredient is explained.

Manufacture of medicinal preparation using the present compound:

The clinical dose level of the present compound is 60 to 6,000 mg/60 kg b.w./day, preferably 100 to 3,000 mg/60 kg/day. The daily dose is divided into 3 parts and administered three times/day with one part/time. The route of administration may be oral or injection, however, in consideration of the long term-administration, oral administration is preferable.

On manufacturing the medicinal preparations, the present compound may be used as a composition with a pharmaceutically acceptable carrier.

The form and shape of the medicinal preparation include tablets, sugar-coated tablets, pills, capsules, powders, granules, troches, liquids, suppositories and injections.

As a carrier thereof, lactose, sucrose, sorbitol, mannitol, potato-starch, corn-starch, amyropectine, other various starches, derivatives of cellulose, for instance, carboxymethylcellulose, methylcellulose, gelatin, magnesium stearate, calcium stearate, polyvinyl alcohol, polyethylene glycol wax, gum arabic, talc, titanium dioxide, vegetable oil such as olive oil, peanut oil and sesame oil, paraffin oil, neutral fatty bases, ethanol, an aqueous physiological saline solution, sterilized water, glycerol, colouring agents, seazonings, thickening agents, stabilizers, isotonic agents and buffer solutions are possibly mentioned.

The content of one of the present compounds in the above-mentioned medicinal preparations is 0.1 to 90% by weight, preferably 1 to 60% by weight of the preparation.

In addition to the above-mentioned anti-peptic ulcer activity, the present compound has actions of suppressing hyperacidity, of dilating peripheral vessels and bronchi and of reducing blood pressure, and anti-arrhythmic action and anti-inflammatory action.

The followings concern Examples, however, it should be understood that these Examples are for the concrete explanation of the present invention, but not for limiting the scope of the present invention:

EXAMPLE 1

Synthesis of 2-(3,4,5-trimethoxyphenyl)-4-methyl-5-acetylthiazole

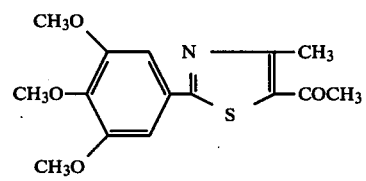

Into 200 ml of benzene, 22.7 g (0.1 mol) of 3,4,5-trimethoxythiobenzamide and 16.0 g (0.12 mol) of 1-acetyl-1-chloroacetone were dissolved, and the solution was heated under a reflux condenser for 3 hours. The crystals, which separated out after cooling the reaction mixture, were recrystallized from methanol to obtain 24.5 g of pale yellow needle-like crystals of the product melting at 128° to 129° C. The yield was 79.8%. The method belongs to the above-mentioned method (a).

Results of elementary analysis (%):

|  | C | H | N | S |
|---|---|---|---|---|
| Calculated as $C_{15}H_{17}O_4SN$: | 58.63 | 5.54 | 4.56 | 10.42 |
| Found: | 58.59 | 5.56 | 4.57 | 10.45 |

EXAMPLE 2

Synthesis of 2-(3,4,5-trimethoxyphenyl)-4-methylthiazole

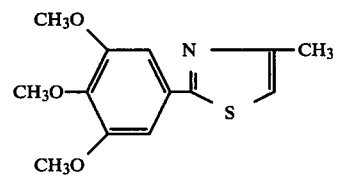

Into 200 ml of benzene, 22.7 g (0.1 mol) of 3,4,5-trimethoxythiobenzamide and 11.1 g (0.12 mol) of chloroacetone were dissolved, and the solution was heated under a reflux condenser for 5 hours. After cooling to room temperature, the crystals which separated out were collected by filtering and recrystallized from methanol. The product consisting of pale yellow needle-like crystals, and amounting to 16.5 g was thus obtained, melting at 105° to 106.5° C. The yield was 62%.

Results of elementary analysis (%):

| | C | H | N | S |
|---|---|---|---|---|
| Calculated as C₁₃H₁₅NO₃S: | 58.85 | 5.70 | 5.28 | 12.08 |
| Found: | 58.86 | 5.68 | 5.26 | 12.06 |

EXAMPLE 3

Synthesis of 2-(3,4,5-trimethoxyphenyl)-4-methylthiazole-5-carboxylic acid ethyl ester

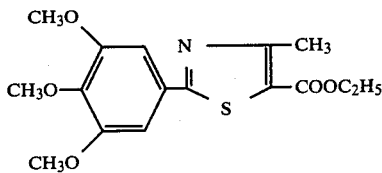

In a round bottom flask, 21.1 g (0.1 mol) of 3,4,5-trimethoxybenzamide, 4.4 g (0.02 mol) of diphosphorus pentasulfide and 250 ml of chloroform were introduced and after attaching a reflux condenser to the flask, the content was heated for 2 hours while refluxing. Then, 19.8 g (0.12 mol) of alphachloroacetoacetic ethyl ester was added to the content of the flask, and the mixture was heated for 5 hours while refluxing. After filtering the reaction mixture while hot and condensing the filtrate to dryness, activated carbon was added to the residue and the mixture was recrystallized from ethanol. The product consisting of needle-like crystals light cream in colour amounting to 28.2 g was thus obtained at a yield of 84%. The crystals melted at 118° to 119° C.

Results of elementary analysis (%):

| | C | H | N | S |
|---|---|---|---|---|
| Calculated as C₁₆H₁₉NO₅S: | 56.94 | 5.64 | 4.15 | 9.51 |
| Found: | 56.95 | 5.66 | 4.15 | 9.53 |

N.B. This method belongs to the above-mentioned method (a), however, of the latter one therein.

EXAMPLE 4

Synthesis of 2-(3,4,5-trimethoxyphenyl)-4-methylthiazole-5-carboxylic acid

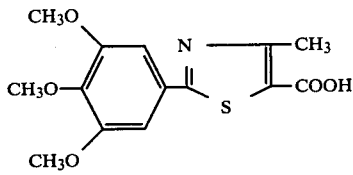

Ethyl 2-(3,4,5-trimethoxyphenyl)-4-methyl-thiazolecarboxylate (10.1 g corresponding to its 0.03mol), 150 ml of ethanol and 50 ml of an aqueous 10% solution of sodium hydroxide were heated for 1.5 hours under a reflux condenser. After condensing the reaction mixture to 40 ml and neutralizing the condensate with 6 N hydrochloric acid, the precipitate which separated was washed with water and recrystallized from an aqueous 50% ethanolic solution to obtain the product amounting to 8.3 g, consisting of faintly yellow needle-like crystals, melting at 205° to 207° C. at a yield of 90%.

Results of elementary analysis (%):

| | C | H | N | S |
|---|---|---|---|---|
| Calculated as C₁₄H₁₅NO₅S: | 54.36 | 4.89 | 4.53 | 10.36 |
| Found: | 54.39 | 4.87 | 4.52 | 10.39 |

EXAMPLE 5

Synthesis of 2-(3,4,5-trimethoxyphenyl)-4-methylthiazole-5-carboxylic acid hydrazide

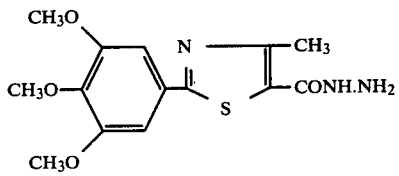

Ethyl 2-(3,4,5-trimethoxyphenyl)-4-methylthiazole-5-carboxylate prepared in Example 4 (6.2 g corresponding to its 0.02 mol), 6.1 g (0.1 mol) of hydrazine hydrate of purity of 82% and 150 ml of ethanol were heated for 6 hours at a temperature of 90° C. The crystals, which separated out after cooling the reaction mixture, were recrystallized from 95% aqueous ethanolic solution to obtain the object consisting of faintly yellow scale-like crystals, amounting to 3.8 g and melting at 179.5° to 181° C. at a yield of 59%.

Results of elementary analysis (%):

| | C | H | N | S |
|---|---|---|---|---|
| Calculated as C₁₄H₁₇N₃O₄S: | 52.00 | 5.29 | 13.00 | 9.91 |
| Found: | 52.03 | 5.28 | 13.02 | 9.95 |

EXAMPLE 6

Synthesis of 2-(3,4,5-trimethoxyphenyl)-4-methyl-5-acetylthiazole-oxime

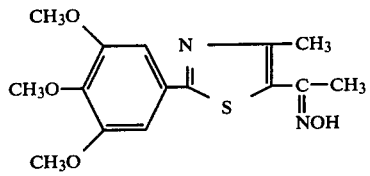

Into an ethanolic solution of 3.1 g (0.01 mol) of 2-(3,4,5-trimethoxyphenyl)-4-methyl-5-acetylthiazole obtained in Example 1 dissolved in 50 ml of ethanol, 27 ml of an aqueous 2% solution of sodium hydroxide (0.013 mol) and 0.93 g (0.013 mol) of hydroxylamine hydrochlorinate were added, and the mixture was heated for 3 hours under a reflux condenser. After cooling the mixture to room temperature, the cooled mixture was introduced into 800 ml of iced water.

The thus precipitated material was collected by filtration and the precipitate was recrystallized from an 80% aqueous ethanolic solution to obtain the product consisting of pale yellow micro-needle-like crystals amounting to 2.1 g corresponding to a yield of 65% and melting at 161.5° to 163° C.

The results of elementary analysis (%):

|  | C | H | N | S |
|---|---|---|---|---|
| Calculated as $C_{15}H_{18}N_2O_4S$: | 55.89 | 5.63 | 8.69 | 9.94 |
| Found: | 55.91 | 5.61 | 8.68 | 9.90 |

EXAMPLE 7

Synthesis of 2-(3,4,5-trimethoxyphenyl)-4-methyl-5-acetylthiazole-oximeacetate

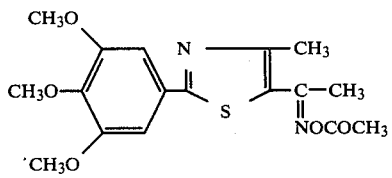

2-(3,4,5-trimethoxyphenyl)-4-methyl-5-acetyl-thiazole-oxime prepared in Example 6 (1.6 g corresponding to 0.005 mol) was dissolved in 30 ml of acetic acid, and 0.8 g of sodium acetate and 2 g of acetic anhydride (0.02 mol) were added to the solution. The whole mixture was heated at a temperature of 90° C. for 5 hours, and after cooling to room temperature, the reaction mixture was introduced into 100 ml of iced water. Upon leaving, a precipitate separated. The precipitate was collected by filtration, washed with water and recrystallized with ethanol to obtain the object consisting of faintly yellow scale-like crystals amounting to 1.5 g melting at 158° to 159° C. at a yield of 83%.

Results of elementary analysis (%):

|  | C | H | N | S |
|---|---|---|---|---|
| Calculated as $C_{17}H_{20}N_2O_5S$: | 56.03 | 5.53 | 7.69 | 8.80 |
| Found: | 56.06 | 5.51 | 7.70 | 8.76 |

EXAMPLE 8

Synthesis of 2-(3,4,5-trimethoxyphenyl)-4-methyl-5-acetylthiazole-semicarbazone

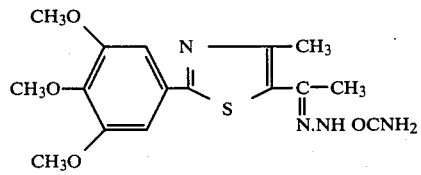

2-(3,4,5-trimethoxyphenyl)-4-methyl-5-acetylthiazole (3.7 g corresponding to its 0.012 mol) was dissolved into 50 ml of ethanol, and 32 ml of an aqueous 2% solution of sodium hydroxide (0.013 mol) and 1.8 g (0.016 mol) of semicarbazide hydrochloride were added to the solution. The whole mixture was then heated for 5 hours under a reflux condenser. After cooling the reaction mixture to room temperature, the mixture was introduced into one liter of iced water. The precipitate which separated was collected by filtration, washed with water and was recrystallized from ethanol to obtain the object consisting of yellow needle-like crystals amounting to 3.0 g and melting at 240° to 242° C. The yield was 69%.

Results of elementary analysis (%):

|  | C | H | N | S |
|---|---|---|---|---|
| Calculated as $C_{16}H_{20}N_4O_4S$: | 52.75 | 5.53 | 15.37 | 8.80 |
| Found: | 52.71 | 5.53 | 15.35 | 8.83 |

EXAMPLE 9

Synthesis of 2-(3,4,5-trimethoxyphenyl)-4-methyl-5-acetylthiazole-thiosemicarbazone

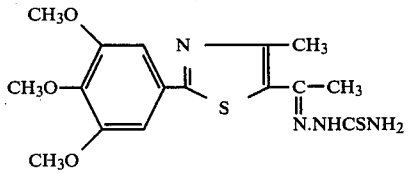

2-(3,4,5-trimethoxyphenyl)-4-methyl-5-acetylthiazole prepared in Example 1 (1.0 g corresponding to its 0.0033 mol) was dissolved in 30 ml of ethanol, and to the solution, 8.6 ml of an aqueous 2% solution of sodium hydroxide (0.0045 mol) and 0.4 g (0.0044 mol) of thiosemicarbazide were added, and the mixture was heated for 3 hours under a reflux condenser. After cooling the reaction mixture, it was introduced into 300 ml of iced water, and the precipitate which separated was collected by filtration. After washing the precipitate with water, it was recrystallized from ethanol to obtain the object consisting of yellow needle-like crystals amounting to 0.82 g at a yield of 65%, which decomposed at 209° to 212° C.

Results of elementary analysis (%):

|  | C | H | N | S |
|---|---|---|---|---|
| Calculated as $C_{16}H_{20}N_4O_3S_2$: | 50.51 | 5.30 | 14.73 | 16.85 |
| Found: | 50.48 | 5.30 | 14.72 | 16.87 |

EXAMPLE 10

Synthesis of 2-(3,4,5-trimethoxyphenyl)-4-methyl-5-acetylthiazole-guanylhydrazone

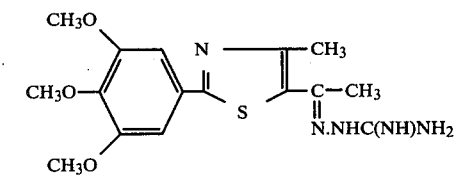

A mixture of 2.2 g (0.007 mol) of 2-(3,4,5-trimethoxyphenyl)-4-methyl-5-acetylthiazole obtained in Example 1, 2.1 g of aminoguanidine sulfate (0.008 mol) and 200 ml of ethanol was heated for 6 hours under a reflux condenser. After cooling the reaction mixture to room temperature, the precipitate which separated was collected by filtration and was recrystallized from a 95% ethanol to obtain 1.2 g of yellow micro-needle-like crystals melting at a higher temperature than 260°. This product is a sulfate of 2 mols of the object.

Results of elementary analysis (%):

|  | C | H | N | S |
|---|---|---|---|---|
| Calculated as |  |  |  |  |
| $(C_{16}H_{21}N_5O_3)_2 \cdot H_2SO_4$: | 46.59 | 5.38 | 16.98 | 11.65 |
| Found: | 46.57 | 5.37 | 16.97 | 11.69 |

EXAMPLE 11

Synthesis of 2-(3,4,5-trimethoxyphenyl)-4,5-dimethylthiazole

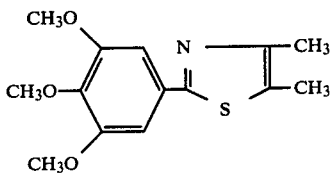

The same procedures as in Example 2 except for using 3-chlorobutanone-2 instead of chloroacetone in Example 2 were carried out to obtain the object at a yield of 65%. The product melts at 93° to 94° C. and consists of colourless needle-like crystals.

Results of elementary analysis (%):

|  | C | H | N | S |
|---|---|---|---|---|
| Calculated as $C_{14}H_{17}NO_3S$: | 60.20 | 6.13 | 5.01 | 11.48 |
| Found: | 60.22 | 6.12 | 5.01 | 11.51 |

EXAMPLE 12

Synthesis of 2-(3,4,5-trimethoxyphenyl)-4-ethyl-5-methylthiazole

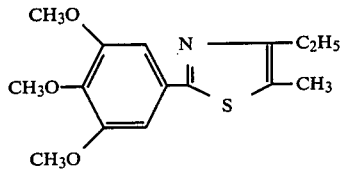

The same procedures except for using 4-chloro-3-pentanone instead of chloroacetone as in Example 1 were carried out in Example 12. The yield was 77%. The product consists of colourless micro-needle-like crystals melting at 91° to 92° C.

Results of elementary analysis (%):

|  | C | H | N | S |
|---|---|---|---|---|
| Calculated as $C_{15}H_{19}NO_3S$: | 61.41 | 6.53 | 4.77 | 10.93 |
| Found: | 61.39 | 6.54 | 4.78 | 10.90 |

EXAMPLE 13

Synthesis of 2-(3,4,5-trimethoxyphenyl)-4-methylthiazole-5-carboxylic acidamide

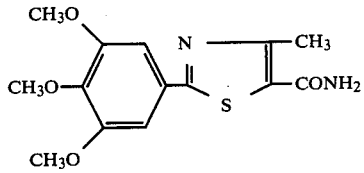

Into 200 ml of methanol, 16.9 g (0.05 mol) of 2-(3,4,5-trimethoxyphenyl)-4-methylthiazole-5-carboxylic acid ethyl ester produced in Example 3 was dissolved, and 25 ml of an aqueous 28% solution of ammonia was added to the solution. The mixture was left at room temperature for 7 days, and then condensed to dryness. The dried residue was recrystallized from a mixture of methanol and water to obtain the object amounting to 10.9 g (yield of 71%) consisting of colourless needle-like crystals melting at 196° to 197° C.

Results of elementary analysis (%):

|  | C | H | N | S |
|---|---|---|---|---|
| Calculated as $C_{14}H_{16}N_2O_4S$: | 54.54 | 5.23 | 9.08 | 10.40 |
| Found: | 54.52 | 5.22 | 9.10 | 10.44 |

EXAMPLE 14

Effect of the Present Compound on the Formation of Peptic Ulcer induced by the Artificial Ligature of the Pylorus of Rats Each of a group of male rats consisting of 10 animals was subjected to ligature of the pylorus under anesthesia by ether following the method of Shay et al. after 48 hours fasting (refer to Gastroenterology, 5, 43, 1945).

Just after the ligature, an aqueous suspension of each of the present compounds in an aqueous physiological saline solution was injected to the abdominal cavity of each rat of the group, the rat of control group being injected with an aqueous physiological solution. After keeping the rats under fasting state without supplying water for 15 hours, all rats were sacrificed by ether, and the stomach of each rat was removed to be examined under a microscope for autopsy. The length and breadth of each ulcer, if formed, were measured by mm and each of their product was recorded by $mm^2$, the total sum of the products of 15 animals being divided by 15 to express the degree of occurrence of the peptic ulcer of the group of rats as the ulcer coefficient of the group. The results are shown in Table 1.

In Table 1, the rate of suppression of the formation of peptic ulcer is calculated by the following formula:

$$\text{Rate of suppression of the formation of peptic ulcer (\%)} = \frac{\text{(ulcer coefficient in control group)} - \text{(ulcer coefficient in a treated group)}}{\text{(ulcer coefficient in control group)}} \times 100$$

TABLE 1

Ulcer Coeffiecient and Rate of Suppression
of Formation of Peptic Ulcer
Dose rate: 100 mg/kg body weight

| Compound administered | Ulcer coefficient (mm$^2$) | Rate of Suppression of the Formation of Peptic Ulcer (%) |
|---|---|---|
| Compound of Example 1 | 7.1 | 84.5 |
| Compound of Example 2 | 13.6 | 70.4 |
| Compound of Example 3 | 3.6 | 92.2 |
| Compound of Example 4 | 6.3 | 86.3 |
| Compound of Example 5 | 6.9 | 85.0 |
| Compound of Example 6 | 17.4 | 62.6 |
| Compound of Example 7 | 13.2 | 71.3 |
| Compound of Example 8 | 8.9 | 80.6 |
| Compound of Example 9 | 7.3 | 84.1 |
| Compound of Example 10 | 16.1 | 65.0 |
| Compound of Example 11 | 6.9 | 85.0 |
| Compound of Example 12 | 8.9 | 80.6 |
| Compound of Example 13 | 10.2 | 77.8 |
| Gefarnate[1] | 41.0 | 10.8 |
| None (control) | 46.0 | — |

Note:
Gefarnate, a commercial anti-peptic ulcer medicine with a chemical formula of: 3,7-dimethyl-2,6-octadienyl 5,9,13-trimethyl-4,8,12-tetradecatrienoate.

EXAMPLE 15

Effect of the Present Compound on the Peptic Ulcer induced by Acetic Acid

Each of the respective groups of male rate consisting of 15 animals was subjected to an operation following the method of Okabe et al. (refer to Amer. J. Dig. Dis. 16, 277, 1971) in which a metal circular frame was placed in the region of serosa of the duodenum at 5 to 7 mm from the pylorus under anesthesia by ether, and 0.06 ml of glacial acetic acid was poured from the circular aperture onto he serosal part. After 30 sec., the acetic liquid and the frame was removed in the order.

From third day after the operation, a suspension of each of the present compounds in an aqueous physiological saline solution was administered orally three times a day for consecutive 10 days.

After the administration was over, all rats were sacrificed by ether and their duodenum was removed to be examined under a microscope for autopsy. The length and breadth of each peptic ulcer were measured and the ulcer coefficient was obtained by the same method of calculation as in Example 14. The results are shown in Table 2.

In Table 2, the rate of cure (from peptic ulcer) was calculated by the following formula:

$$\text{Rate of cure (\%)} = \frac{\text{(ulcer coefficient of control group)} - \text{(coefficient of a treated group)}}{\text{(ulcer coefficient of control group)}} \times 100$$

TABLE 2

Ulcer Coeffiecient and Rate of Cure from Peptic Ulcer
Dose rate: 100 mg/kg/day

| Compound administered | Ulcer coefficient (mm$^2$) | Rate of Cure from Peptic Ulcer (%) |
|---|---|---|
| Compound of Example 1 | 1.6 | 79.5 |
| Compound of Example 2 | 1.9 | 74.3 |
| Compound of Example 3 | 1.1 | 85.9 |
| Compound of Example 4 | 1.3 | 83.3 |
| Compound of Example 5 | 1.1 | 85.9 |
| Compound of Example 6 | 3.8 | 51.3 |
| Compound of Example 7 | 1.7 | 78.2 |
| Compound of Example 8 | 1.5 | 76.9 |
| Compound of Example 9 | 3.3 | 57.6 |
| Compound of Example 10 | 3.2 | 60.0 |
| Compound of Example 11 | 1.3 | 83.3 |
| Compound of Example 12 | 1.5 | 76.9 |
| Compound of Example 13 | 2.1 | 73.0 |
| Gefarnate (loc. cit.) | 6.2 | 20.5 |
| Control | 7.8 | 0 |

EXAMPLE 16

The present Example shows a result of sub-acute toxicity test carried out on the present compounds administered to experimental animals as follows:

Experimental animals: both sexes of Sprague-Dowley rats, each weighing 110 to 150 g, 5 weeks after birth at the beginning of the test.

Rearing conditions: each group consisting of 5 males and 5 females; each 5 males or 5 females was kept in an metalwire cage at a room temperature of 22° to 24° C., and RH of 60 to 70% for 3 months with supply of feed and water taken ad lib.

Method of administration: as a representative of the present compounds, 2-(3,4,5-trimethoxyphenyl)-4-methylthiazole-5-carboxylic acid prepared in Example 4 was utilized. The acid was finely pulverized and admixed with a powdery diet commercially available for rats at a level of 0.4% by weight to the diet.

Observation and examination: the intake of the diet per every other day, body weight per week and urinalysis as to sugar, protein, pH and occult blood per month were respectively carried out. After 3 months' rearing, all rats were sacrificed after blood sampling, and autopsied to examine the abnormal findings, if any. Their organs were fixed by formaldehyde, burried in paraffin to be sections of the tissues stained with hematoxylin-eosin. Examinations on collected blood and the prepared sections were also carried out.

Results of the test are as follows:
Intake of diet: as in control group without any abnormal findings,
Body weight gain: as in control group without any abnormal findings,
Mortality: same as above,
Urinalytic results: same as above,
Results of examination of blood: same as above,
Findings on autopsy and on histological examination: same as above.

In the above-mentioned test, the minimal dose rate with which the toxicological signs positively appear could not be obtained, and also the maximal dose rate with which the toxicological signs never appear could not be obtained, while the averaged daily intake of the present compound amounted to 400 mg/kg/day.

EXAMPLE 17

The present example shows an instance wherein granular medicinal preparation containing one of the present compounds suitable for oral administration was prepared.

After mixing 200 g of finely pulverized 2-(3,4,5-trimethoxyphenyl)-4-methylthiazole-5-carboxylic acid and 800 g of corn starch, 80 ml of an aqueous solution of 3 g of carboxymethylcellulose sodium was added to the mixture. The whole mixture was well kneaded and extruded to be glanular shape by an extruding shaping machine. The extruded glanules were dried at a temperature of 60° to 80° C. to be a glanular medicinal preparation.

What is claimed is:

1. 2-(3,4,5-trimethoxyphenyl)-4,5-disubstituted thiazole represented by the formula:

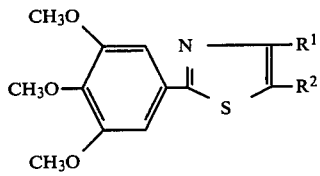

wherein $R^1$ represents an alkyl group of $C_1$ to $C_3$ and $R^2$ represents a hydrogen atom, an alkyl group of $C_1$ to $C_3$, an acetyl group, a carboxyl group of ester group thereof with an alcohol of $C_1$ to $C_3$, a carbamoyl group or a hydrazinocarbonyl group, and wherein the carbonyl group of said acetyl group may also be converted to oxime, oxime-acetate, semicarbazide or guanylhydrazone.

2. 2-(3,4,5-trimethoxyphenyl)-4,5-disubstituted thiazole according to claim 1 wherein said thiazole is represented by the formula:

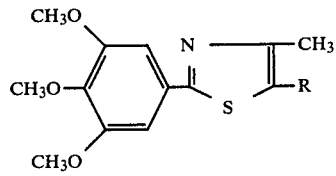

wherein R represents a methyl group, a carboxyl group, an ethoxycarbonyl group, an acetyl group, a carbamoyl group, a hydrazinocarbonyl group or an acetyl group of which the carbonyl group is converted to a thiosemicarbazone.

3. A pharmaceutical composition for treating peptic ulcer in dosage unit form, which comprises an effective amount of a compound of 2-(3,4,5-trimethoxyphenyl)-4,5-disubstituted thiazole represented by the formula:

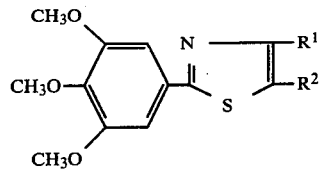

wherein
$R^1$ represents an alkyl group of $C_1$ to $C_3$ and
$R^2$ represents a hydrogen atom, an alkyl group of $C_1$ to $C_3$, an acetyl group, a carboxyl group or an ester group thereof with an alcohol of $C_1$ to $C_3$, a carbamoyl group or a hydrazinocarbonyl group, with the proviso that both $R^1$ and $R^2$ do not represent simultaneously hydrogen atoms, and wherein the carbonyl group of said acetyl group may also be converted to oxime, oxime-acetate, semicarbazide or guanylhydrazone; and a pharmaceutically acceptable carrier or excipient.

4. A pharmaceutical composition of claim 3, wherein the compound of 2-(3,4,5-trimethoxyphenyl)-4,5-disubstituted thiazole is represented by the formula:

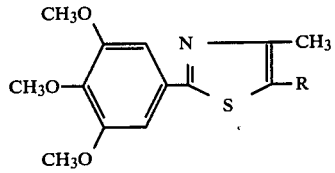

wherein R represents a methyl group, a carboxyl group, an ethoxycarbonyl group, an acetyl group, a carbamoyl group, a hydrazinocarbonyl group or an acetyl group of which the carbonyl group is converted to a thiosemicarbazone.

* * * * *